(12) United States Patent
Naar et al.

(10) Patent No.: US 9,045,749 B2
(45) Date of Patent: Jun. 2, 2015

(54) METHODS TARGETING MIR-128 FOR REGULATING CHOLESTEROL/LIPID METABOLISM

(75) Inventors: Anders M. Naar, Arlington, MA (US); Seyed Hani Najafi-Shoushtari, Brighton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/979,428

(22) PCT Filed: Jan. 13, 2012

(86) PCT No.: PCT/US2012/021257
§ 371 (c)(1),
(2), (4) Date: Oct. 30, 2013

(87) PCT Pub. No.: WO2012/097261
PCT Pub. Date: Jul. 19, 2012

(65) Prior Publication Data
US 2014/0051746 A1    Feb. 20, 2014

Related U.S. Application Data

(60) Provisional application No. 61/432,991, filed on Jan. 14, 2011.

(51) Int. Cl.
| | | |
|---|---|---|
| A61K 48/00 | (2006.01) |
| C12N 15/11 | (2006.01) |
| A61K 31/7088 | (2006.01) |
| A61K 31/7105 | (2006.01) |
| C12N 15/113 | (2010.01) |
| A61K 38/00 | (2006.01) |

(52) U.S. Cl.
CPC ............... *C12N 15/11* (2013.01); *A61K 38/00* (2013.01); *A61K 31/7088* (2013.01); *A61K 31/7105* (2013.01); *C12N 15/113* (2013.01); *C12N 2310/113* (2013.01); *C12N 2310/14* (2013.01); *C12N 2310/3231* (2013.01)

(58) Field of Classification Search
None
See application file for complete search history.

(56) References Cited

U.S. PATENT DOCUMENTS

| 7,307,067 B2 | 12/2007 | Sarnow et al. | |
|---|---|---|---|
| 2005/0059005 A1* | 3/2005 | Tuschl et al. ............ | 435/6 |
| 2006/0019286 A1 | 1/2006 | Horvitz et al. | |

FOREIGN PATENT DOCUMENTS

| WO | 2008/043521 | 4/2008 |
|---|---|---|
| WO | 2009/021235 | 2/2009 |
| WO | 2009/036236 | 3/2009 |
| WO | 2009/132273 | 10/2009 |
| WO | 2010/120508 | 10/2010 |
| WO | 2010/129672 | 11/2010 |

OTHER PUBLICATIONS

Bartel, D.P., "MicroRNAs: target recognition and regulatory functions," Cell, 136 (2):215-233 (2009).
Bauer et al., "Functional validation of new pathways in lipoprotein metabolism identified by human genetics," Curr. Opin. Lipidol., 22 (2):123-128 (2011).
Berger et al., "Genetic variants of insulin receptor substrate-1 (IRS-1) in syndromes of severe insulin resistance. Functional analysis of Ala513Pro and Gly1158Glu IRS-1," Diabet. Med., 19:804-•809 (2002).
Brooks-Wilson et al., "Mutations in ABC1 in Tangier disease and familial high-density lipoprotein deficiency," Nature Genetics, 22:336-45 (1999).
Chen et al., "MicroRNA-125a-5p partly regulates the inflammatory response, lipid uptake, and ORP9 expression in oxLDL-stimulated monocyte/macrophages," Cardiovascular Research, 83:131-139 (2009).
Cuchel and Rader, "Macrophage reverse cholesterol transport: key to the regression of atherosclerosis?" Circulation, 113 (21):2548-2555 (2006).
Eftychi et al., "Analysis of the type 2 diabetes-associated single nucleotide polymorphisms in the genes IRS1, KCNJ11, and PPARG2 in type 1 diabetes," Diabetes, 53:870-873 (2004).
Friedman et al., "Most mammalian mRNAs are conserved targets of microRNAs," Genome Res., 19 (1):92-105 (2009).
The Bovine HapMap Consortium, "Genome-wide survey of SNP variation uncovers the genetic structure of cattle breeds," Science, 324 (5926):528-532 (2009).
Goldstein et al., "The LDL receptor," Arterioscler. Thromb. Vasc. Biol., 29 (4):431-438 (2009).
Hong et al., "ABCA1(Alabama): a novel variant associated with HDL deficiency and premature coronary artery disease," Atherosclerosis, 164: 245-250 (2003).
Ma et al., "Genome-wide association analysis of total cholesterol and high-density lipoprotein cholesterol levels using the Framingham heart study data," BMC Med Genet 11, 55 (2010).
Matkovich et al., "Reciprocal Regulation of Myocardial microRNAs and Messenger RNA in Human Cardiomyopathy and Reversal of the microRNA Signature by Biomechanical Support," Circulation, 119:1263-1271 (2009).
Muiños-Gimeno et al., "Design and evaluation of a panel of single-nucleotide polymorphisms in microRNA genomic regions for association studies in human disease," Eur. J. Hum. Genet. 18:218-26 (2010).
Najafi-Shoushtari et al., "MicroRNA-33 and the SREBP host genes cooperate to control cholesterol homeostasis," Science, 328 (5985):1566-1569 (2010).
Rader et al, "The role of reverse cholesterol transport in animals and humans and relationship to atherosclerosis," J. Lipid Res., 50 Suppl:S189-194 (2009).
Sabeti et al., "Genome-wide detection and characterization of positive selection in human populations," Nature, 449 (7164):913-918 (2007).

(Continued)

*Primary Examiner* — Kimberly Chong
(74) *Attorney, Agent, or Firm* — Fish & Richardson P.C.

(57) ABSTRACT

Methods for targeting microRNA 128 (miR-128) for regulating cholesterol/lipid metabolism and insulin sensitivity.

20 Claims, 11 Drawing Sheets

(56) References Cited

OTHER PUBLICATIONS

Silander et al., "Gender differences in genetic risk profiles for cardiovascular disease," PLoS One, 3:e3615 (2008).
Tall et al., "HDL, ABC transporters, and cholesterol efflux: implications for the treatment of atherosclerosis," Cell Metab., 7(5):365-375 (2008).
Teslovich et al, "Biological, clinical and population relevance of 95 loci for blood lipids," Nature, 466:707-713 (2010).
Thum et al., "MicroRNAs in the Human Heart: A Clue to Fetal Gene Reprogramming in Heart Failure," Circulation, 116:258-267 (2007).
Van Rooij et al., "Dysregulation of microRNAs after myocardial infarction reveals a role of miR-29 in cardiac fibrosis," PNAS, 105(35):13027-13032 (2008).
Walker et al, "Conserved role of SIRT1 orthologs in fasting-dependent inhibition of the lipid/cholesterol regulator SREBP," Genes Dev., 24:1403-1417 (2010).
Walldius and Jungner, "The apoB/apoA-I ratio: a strong, new risk factor for cardiovascular disease and a target for lipid-lowering therapy—a review of the evidence," J. Intern. Med., 259 (5):493-519 (2006).
Wang et al., "Biliary lipids and cholesterol gallstone disease," J Lipid Res., 50:S406-411 (2009).
International Preliminary Report on Patentability issued in PCT/US2012/021257 on Jul. 16, 2013 (5 pages).
International Search Report and Written Opinion mailed May 29, 2012 in international application No. PCT/US2012/021257, 5 pgs.
Extended European Search Report issued in EP12734471.1 on Jun. 30, 2014 (10 pages).
Office Action issued in EP12734471.1 on Mar. 25, 2015 (8 pp.).

* cited by examiner

FIG. 1

```
LOCUS       NR_029672                 82 bp    RNA     linear   PRI 19-DEC-2010
DEFINITION  Homo sapiens microRNA 128-1 (MIR128-1), microRNA.
ACCESSION   NR_029672
VERSION     NR_029672.1  GI:262205268
FEATURES             Location/Qualifiers
     source          1..82
                     /organism="Homo sapiens"
                     /mol_type="transcribed RNA"
                     /db_xref="taxon:9606"
                     /chromosome="2"
                     /map="2q21.3"
     gene            1..82
                     /gene="MIR128-1"
                     /gene_synonym="MIR128A; MIRN128-1; MIRN128A"
                     /note="microRNA 128-1"
                     /db_xref="GeneID:406915"
                     /db_xref="HGNC:31510"
                     /db_xref="MIM:611774"
                     /db_xref="miRBase:MI0000447"
     exon            1..82
                     /gene="MIR128-1"
                     /gene_synonym="MIR128A; MIRN128-1; MIRN128A"
                     /inference="alignment:Splign"
                     /number=1
     ncRNA           50..70
                     /gene="MIR128-1"
                     /gene_synonym="MIR128A; MIRN128-1; MIRN128A"
                     /ncRNA_class="miRNA"
                     /product="hsa-miR-128"
                     /db_xref="miRBase:MIMAT0000424"
                     /db_xref="GeneID:406915"
                     /db_xref="HGNC:31510"
                     /db_xref="MIM:611774"
                     /db_xref="miRBase:MI0000447"
ORIGIN
        1 tgagctgttg gattcggggc cgtagcactg tctgagaggt ttacatttct cacagtgaac
       61 cggtctcttt ttcagctgct tc   (SEQ ID NO:1)
```

FIG. 2 tcacagtgaaccggtctctttt  (SEQ ID NO:2)

ucacagugaaccggucucuuu  (SEQ ID NO:3)

FIG. 3

```
      u    u      uuc       uag      cu        u
   gagc guugga ggggccg   cacugu  gagaggu  u
   |||| |||||| |||||||   ||||||  |||||||
   uucg cgacuu cucuggc   gugaca  cucuuua  a
      c    u      uuu       caa      --       c
```

(SEQ ID NO:4)

FIG. 4

```
LOCUS       NR_029824               84 bp    RNA     linear   PRI 20-SEP-2010
DEFINITION  Homo sapiens microRNA 128-2 (MIR128-2), microRNA.
ACCESSION   NR_029824
VERSION     NR_029824.1  GI:262206021
FEATURES             Location/Qualifiers
     source          1..84
                     /organism="Homo sapiens"
                     /mol_type="transcribed RNA"
                     /db_xref="taxon:9606"
                     /chromosome="3"
                     /map="3p22.3"
     gene            1..84
                     /gene="MIR128-2"
                     /gene_synonym="mir-128b; MIR128B; MIRN128-2; MIRN128B"
                     /note="microRNA 128-2"
                     /db_xref="GeneID:406916"
                     /db_xref="HGNC:31511"
                     /db_xref="MIM:611769"
                     /db_xref="miRBase:MI0000727"
     exon            1..84
                     /gene="MIR128-2"
                     /gene_synonym="mir-128b; MIR128B; MIRN128-2; MIRN128B"
                     /inference="alignment:Splign"
                     /number=1
     ncRNA           52..72
                     /gene="MIR128-2"
                     /gene_synonym="mir-128b; MIR128B; MIRN128-2; MIRN128B"
                     /ncRNA_class="miRNA"
                     /product="hsa-miR-128"
                     /db_xref="miRBase:MIMAT0000424"
                     /db_xref="GeneID:406916"
                     /db_xref="HGNC:31511"
                     /db_xref="MIM:611769"
                     /db_xref="miRBase:MI0000727"
ORIGIN
        1 tgtgcagtgg gaaggggggc cgatacactg tacgagagtg agtagcaggt ctcacagtga
       61 accggtctct ttccctactg tgtc     (SEQ ID NO:5)
```

FIG. 5

```
u  ug        a              aua       ac    g gag
 g  caguggg agggggccg    cacugu   gaga u   u
 |  ||||||| |||||||||    ||||||   |||| |
 u  gucaucc uuucucuggc   gugaca   cucu g   a
 c  gu       c            caa      --   g acg
```

(SEQ ID NO:6)

The RAB3GAP1-R3HDM1-LCT locus

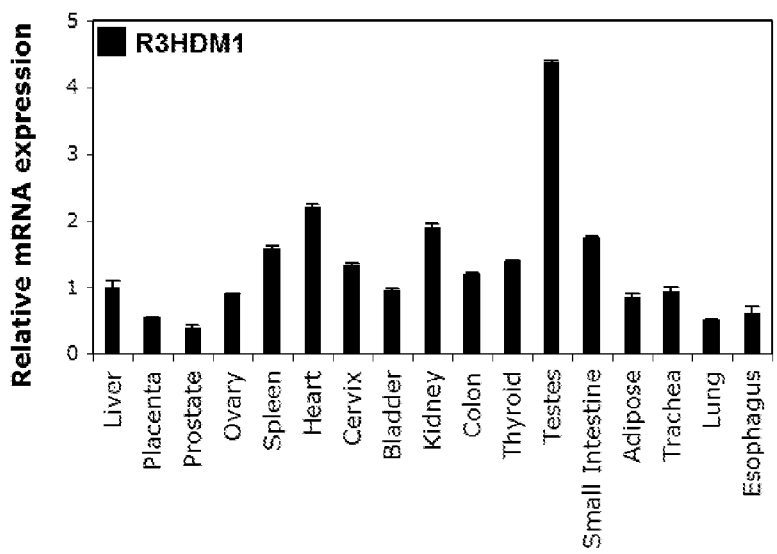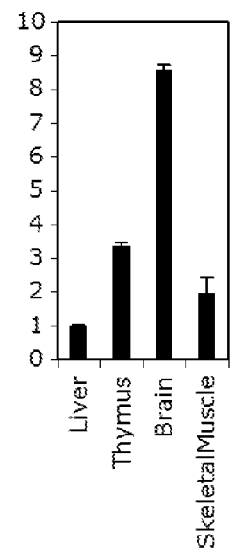
FIG. 7A
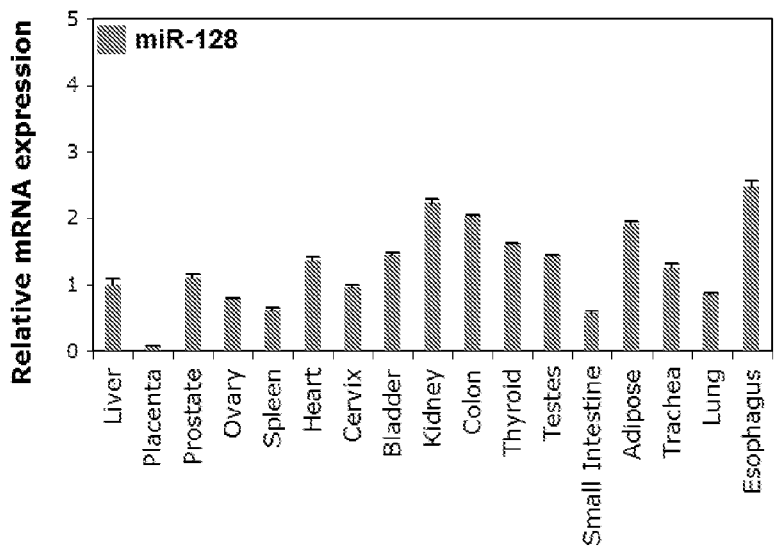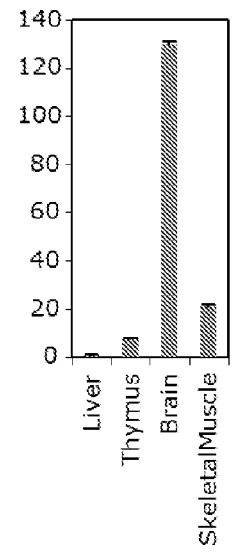
FIG. 7B

FIG. 8A
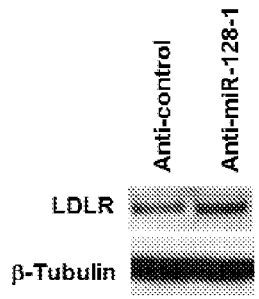
FIG. 8B
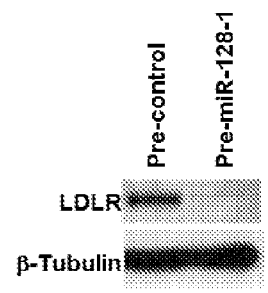
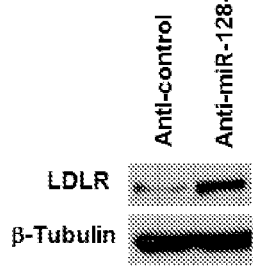
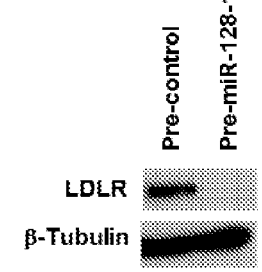
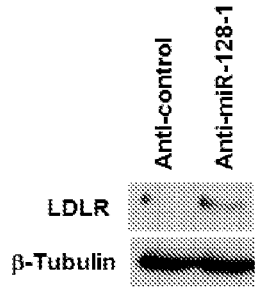
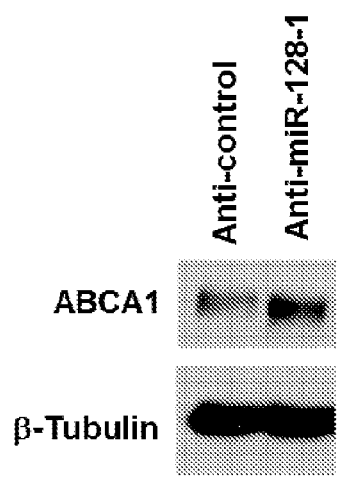
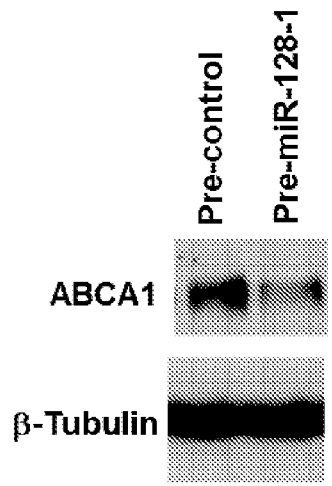
FIG. 9A
FIG. 9B

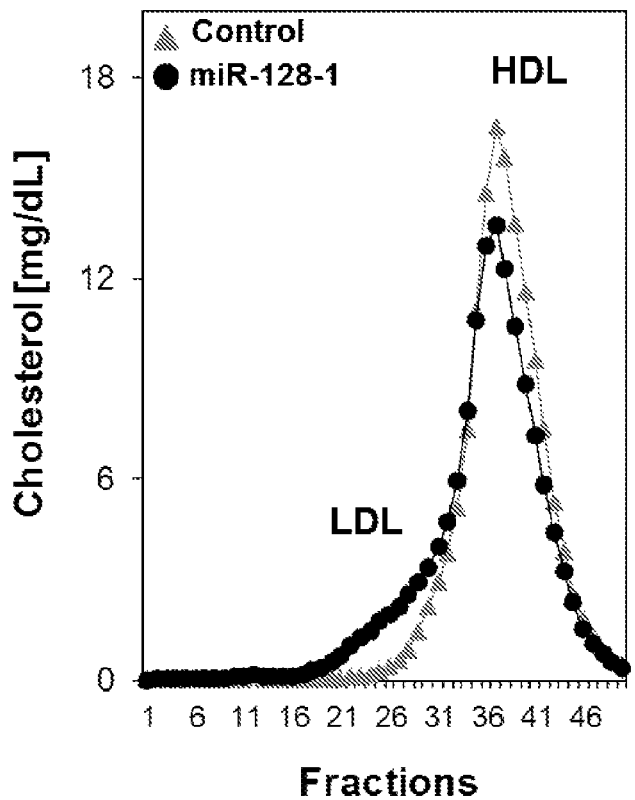

FIG. 17B

```
TCACTGCATATAAGGAGTGTGGTATAGTATAAAGAAACTTTCTGCAGGTAG
TAATTATAGTGAAGATTTTAGGTTTACAAAGCCCTAGCTGTTTTCTGTGTA
GCTTTTATTATTCTTATGACTCTTGACAAGTTTGTAGCTTCACCATATACA
TTTAATATTTTGCAATAATTGGCCTTGTTCCTGAGCTGTTGGATTCGGGGC
CGTAGCACTGTCTGAGAGGTTTACATTTCTCACAGTGAACCGGTCTCTTTT
TCAGCTGCTTCCTGGCTTCTTTTTACTCAGGTTTCCACTGCTTTTTGCTT
TTTTTAATGCTGTATGAAGGTGTTAACATTTGTTTATATTTTTCATTAATT
GTAATACCTTTAAATCATGCATCATACTCAGAAATAGGGATTAGAATTTAA
GTGACATCTTTGGCCTAATATAATTTACCTGTTAAAAATTTGTGAAAGCTA
TTGCTTATTTCTTTTCCAAAGTAGATTTGGATGA    (SEQ ID NO:8)
```

METHODS TARGETING MIR-128 FOR REGULATING CHOLESTEROL/LIPID METABOLISM

CLAIM OF PRIORITY

This application is a U.S. National Phase Application under 35 U.S.C. 371 of International Patent Application No. PCT/US2012/021257, filed on Jan. 13, 2012, which claims the benefit of U.S. Provisional Application Ser. No. 61/432, 991, filed on Jan. 14, 2011. The entire contents of the foregoing are incorporated herein by reference.

FEDERALLY SPONSORED RESEARCH OR DEVELOPMENT

This invention was made with Government support under Grants No. R21DK084459 awarded by the National Institutes of Health. The Government has certain rights in the invention.

TECHNICAL FIELD

This invention relates to methods for targeting microRNA-128 (miR-128) for regulating cholesterol/lipid metabolism and insulin sensitivity, inter alia.

BACKGROUND

Abnormal cholesterol and lipid homeostasis are linked with prevalent diseases such as metabolic syndrome, atherosclerosis/cardiovascular disease, and type 2 diabetes. Cholesterol and lipids are trafficked in the blood as lipoprotein particles, such as low-density lipoprotein (LDL) and high-density lipoprotein (HDL) that ferry their fatty cargo to different cells and tissues. Excess circulating LDL can be oxidized and taken up by arterial macrophages, turning them into cholesterol/lipid-filled "foam cells" that are involved in the formation of atherosclerotic plaques. Triglycerides, as major components of very-low-density lipoprotein (VLDL), have been linked to atherosclerosis, and, by extension, the risk of heart disease and stroke. Elevated, triglycerides (e.g., mildly elevated fasting levels, above 150 mg/dL (1.7 mmol/L), or high fasting levels above 200 mg/dL (2.26 mmol/L)) are common in subjects with metabolic syndrome/insulin resistance and those with poorly controlled diabetes, and contribute to the risk of atherosclerosis, heart disease, and stroke in that population.

SUMMARY

As shown herein, miR-128-1 targets a large number of genes/proteins involved in cholesterol/lipid homeostasis and insulin signaling. The data presented herein demonstrates that low density lipoprotein receptor (LDLR), ATP-binding cassette, sub-family A (ABC1), member 1 (ABCA1), Sirtuin 1 (SIRT1), and Insulin Receptor Substrate 1 (IRS1) are regulated by miR-128-1. Indeed, antisense targeting of miR-128-1 in human liver cells (HepG2) results in increased expression of these key cholesterol/lipid regulators and insulin signaling proteins. Dys-regulation of these proteins in humans is thought to contribute to aberrant cholesterol/lipid homeostasis and insulin resistance in Metabolic Syndrome and cardiovascular disease patients. Thus, the methods described herein can be used to normalize cholesterol/lipid homeostasis and decrease insulin resistance. For example, in some embodiments the methods described herein include the use of inhibitory nucleic acids to target miR-128-1 to improve cholesterol/lipid homeostasis and insulin resistance, e.g., in subjects with Metabolic Syndrome and/or cardiovascular disease.

Thus, in a first aspect, the invention provides methods for reducing levels of serum LDL, reducing levels of serum triglycerides, and/or increasing levels of serum HDL in a subject. The methods include administering to the subject a therapeutically effective amount of an inhibitory nucleic acid that is complementary to all or part of any of SEQ NOs:1-6, e.g., to all or part of SEQ ID NO:2.

In another aspect, the invention provides methods for treating or reducing the risk of developing diabetic neuropathy, non-alcoholic fatty liver disease, non-alcoholic steatohepatitis, atherosclerosis, and/or cardiovascular disease in a subject. The methods include administering to the subject a therapeutically effective amount of an inhibitory nucleic acid that is complementary to all or part of any of SEQ NOs:1-6, e.g., to all or part of SEQ NO:2.

In an additional aspect, the invention provides methods for reducing obesity, treating or reducing predisposition to insulin resistance, and/or treating or reducing predisposition to type II diabetes, in a subject. The methods include administering to the subject an inhibitory nucleic acid sequence that is complementary to all or part of any of SEQ NOs:1-6, e.g., to all or part of SEQ NO:2, thereby decreasing obesity in the subject.

In a further aspect, the invention provides methods for increasing uptake of lipids or cholesterol by a cell, e.g., a liver cell, or for increasing sensitivity of a cell, e.g., a liver cell, to insulin. The methods include contacting the cell with an inhibitory nucleic acid sequence that is complementary to all or part of any of SEQ NOs:1-6, e.g., to all or part of SEQ ID NO:2.

In some embodiments of the methods described herein, the inhibitory nucleic acid is complementary to at least nucleotides 2-7 (5'-CACAGU-3') of SEQ ID NO:3. In some embodiments of the methods described herein, the inhibitory nucleic acid can be designed to target nucleotides 2-10 of the mature miR-128-1 (SEQ NO:3), e.g., complementary to CACAGUGAA, e.g., have the sequence TTCACTGTG (SEQ ID NO:9, which is the same as nucleotides 12-20 of SEQ NO:7).

In some embodiments of the methods described herein, the inhibitory nucleic acid comprises all or part of AAAGAGAC-CGGTTCACTGTGA (SEQ ID NO:7).

In some embodiments of the methods described herein, the inhibitory nucleic acid is an antisense oligonucleotide. In some embodiments, the antisense oligonucleotide comprises a sequence that is complementary to SEQ ID NO:3.

In some embodiments of the methods described herein, the inhibitory nucleic acid has one or more chemical modifications to the backbone or side chains as described herein. In some embodiments of the methods described herein, the inhibitory nucleic acid is an antagomir. In some embodiments of the methods described herein, the inhibitory nucleic acid has at least one locked nucleotide, and/or has a phosphorothioate backbone.

In some embodiments of the methods described herein, the inhibitory nucleic acid is an interfering RNA. In some embodiments, the interfering RNA is a small hairpin RNA (shRNA) or small interfering RNA (siRNA).

In some embodiments of the methods described herein, the inhibitory nucleic acid sequence inhibits post-transcriptional processing of SEQ ID NO:1 or 5.

In some embodiments of the methods described herein, the subject has metabolic syndrome or Type 2 diabetes.

In some embodiments of the methods described herein, the methods include selecting a subject on the basis that they have metabolic syndrome or Type 2 diabetes.

In some embodiments of the methods described herein, the methods include detecting the presence of one or more alleles associated with increased, levels of miR-128 and/or predisposition to increased levels of serum lipids, and optionally selecting a subject on the basis of the presence of an allele associated with increased levels of miR-128.

In some embodiments of the methods described herein, the methods include determining a level of triglycerides in the subject, and selecting the subject if they have mildly elevated fasting levels (above 150 mg/dL (1.7 mmol/L)) or high fasting levels above 200 mg/dL (2.26 mmol/L)).

In some embodiments of the methods described herein, the methods include selecting a subject who is in need of weight loss, a subject with a BMI of 25 or above.

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T) (or uracil (U) in the case of RNA), and guanine (G) forms a base pair with cytosine (C)) under suitable conditions of stringency. (See, e.g., Wahl, G. M. and S. L. Berger (1987) Methods Enzymol. 152:399; Kimmel, A. R. (1987) Methods Enzymol. 152:507). For the purposes of the present methods, the inhibitory nucleic acid need not be complementary to the entire sequence, only enough of it to provide specific inhibition; for example in some embodiments the sequence is 100% complementary to at least nucleotides (nts) 2-7 or 2-8 at the 5' end of the microRNA itself (e.g. the 'seed sequence'), e.g., nts 2-7 or 2-8 of SEQ ID NOs:2 or 3. Further details are provided below.

As used herein, an "antisense oligonucleotide" refers to a nucleic acid sequence that is complementary to a DNA or RNA sequence, such as that of a microRNA.

"RNA" is a molecule comprising at least one or more ribonucleotide residues. A "ribonucleotide" is a nucleotide with a hydroxyl group at the 2' position of a beta-D-ribofuranose moiety. The term RNA, as used herein, includes double-stranded RNA, single-stranded RNA, isolated RNA, such as partially purified RNA, essentially pure RNA, synthetic RNA, recombinantly produced RNA, as well as altered RNA that differs from naturally occurring RNA by the addition, deletion, substitution and/or alteration of one or more nucleotides. Nucleotides of the RNA molecules can also comprise non-standard nucleotides, such as non-naturally occurring nucleotides or chemically synthesized nucleotides or deoxynucleotides.

A "microRNA" (miRNA) is a single-stranded RNA molecule of about 21-23 nts in length. In general, miRNAs regulate gene expression. miRNAs are encoded by genes from whose DNA they are transcribed, but miRNAs are not translated into protein. Each primary miRNA transcript is processed into a short stem-loop structure (see, e.g., FIG. 3) before undergoing further processing into a functional miRNA. Mature miRNA molecules are partially complementary to one or more messenger RNA (mRNA) molecules, and their main function is to down-regulate gene expression.

As used herein "an interfering RNA" refers to any double stranded or single stranded RNA sequence, capable—either directly or indirectly (i.e., upon conversion)—of inhibiting or down regulating gene expression by mediating RNA interference. Interfering RNA includes but is not limited to small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

A "small interfering RNA" or "siRNA" as used herein refers to any small RNA molecule capable of inhibiting or down regulating gene expression by mediating RNA interference in a sequence specific manner. The small RNA can be, for example, about 18 to 21 nucleotides long.

As used herein, an "antagomir" refers to a small synthetic RNA having complementarity to a specific microRNA target, with either mispairing at the cleavage site or one or more base modifications to inhibit cleavage.

As used herein, the phrase "post-transcriptional processing" refers to mRNA processing that occurs after transcription and is mediated, for example, by the enzymes Dicer and/or Drosha.

By "an effective amount" is meant the amount of a required agent or composition comprising the agent to ameliorate the symptoms of a disease relative to an untreated patient. The effective amount of composition(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

As used herein, "cholesterol homeostasis" refers to the regulation of cholesterol uptake, cholesterol biosynthesis, cholesterol conversion to bile acids and excretion of bile acids as such processes occur in a subject having healthful levels of LDL, HDL and cholesterol in the blood (e.g., such healthful levels are also referred to herein as a "reference standard"). Accordingly, a subject in need of cholesterol homeostasis is in need of improved regulation resulting in a return to healthful levels of LDL, HDL and/or cholesterol in the blood.

A "subject" is a vertebrate, including any member of the class mammalia, including humans, domestic and farm animals, and zoo, sports or pet animals, such as mouse, rabbit, pig, sheep, goat, cattle and higher primates. In preferred embodiments the subject is a human.

As used herein, a "vector" or "expression vector" is a nucleic acid-based delivery vehicle comprising regulatory sequences and a gene of interest, which can be used to transfer its contents into a cell.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 shows the sequence of human miR-128-1 precursor, also known as miR-128A precursor (SEQ ID NO:1).

FIG. 2 shows the sequence of mature human miR-128 DNA (SEQ ID NO:2) and RNA (SEQ NO:3). The mature sequences are the same for miR-128-1 and miR-128-2.

FIG. 3 shows the predicted hairpin structure of miR-128-1 precursor RNA (SEQ ID NO:4).

FIG. 4 shows the sequence of human miR-128-2 precursor, also known as miR-128B precursor (SEQ NO:5).

FIG. 5 shows the predicted hairpin structure of miR-128-2 precursor RNA (SEQ ID NO:6).

FIGS. 7A-B are bar graphs showing expression profiles of the miR-128-1 host gene R3HDM1 (7A) and miR-128 (7B) in human tissues. Both genes are shown to be expressed fairly ubiquitously. To the best of the present inventors' knowledge, the function of R3HDM1 has not yet been determined. Additionally, the expression profile of miR-128 reflects the composite expression of both miR-128-1 (located in the R3HDM1 gene) and miR-128-2, whose genomic location is within the ARPP-21 host gene. miR-128-1 and miR-128-2 have identical mature sequences, which are measured here.

FIGS. 8A-B each show the immunoblotting results of three separate experiments demonstrating that introduction of antisense oligonucleotides complementary to human miR-128-1 into human HepG2 liver cells causes increased expression of LDLR (8A), and introduction of human miR-128-1 precursor oligonucleotides into human HepG2 liver cells causes decreased expression of LDLR (8B).

FIGS. 9A-B are each immunoblots showing that introduction of antisense oligonucleotides complementary to human miR-128-1 into human HepG2 liver cells causes increased expression of ABGA1 (9A), and introduction of human miR-128-1 precursor oligonucleotides into HepG2 cells causes decreased expression of ABCA1 (9B). Thus, miR-128-1 is shown to control the expression of ABCA1.

FIGS. 17A-B are line graphs showing that lentiviral-mediated over-expression of miR-128-1 increases the LDL/HDL ratio in mice. FPLC analysis of cholesterol-containing lipoprotein (HDL and LDL) profiles in pooled serum samples from 5-10 mice each in two separate experiments indicate that ectopic miR-128-1 expression alters the distribution of serum HDL and LDL particles while total plasma cholesterol levels were not affected.

FIG. 18 shows the miR-128-1 precursor sequence (bold) including the miR-128-1 guide-strand sequence (underlined) flanked by 200 nt on each side, SEQ ID NO:8.

DETAILED DESCRIPTION

Figure 6:
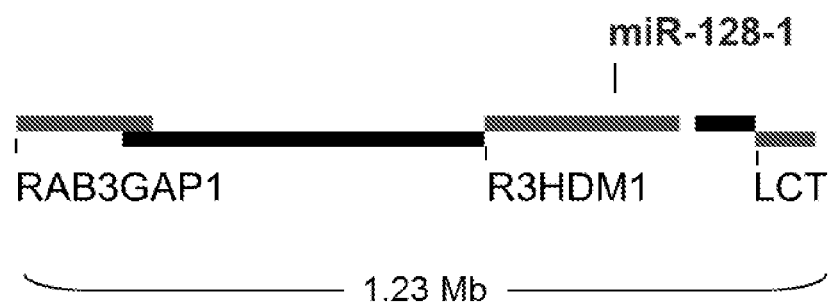
FIG. 6 shows a schematic representation of the RAB3GAP1-R3HDM1-LCT genomic locus harboring miR-128-1 on human chromosome 2. miR-128-1 is located in intron 18 of R3HDM1. The depicted 1.23 Mb genomic region contains the SNPs associated with elevated LDL-C and TC in the analyses in Ma et al.
Figure 10A:
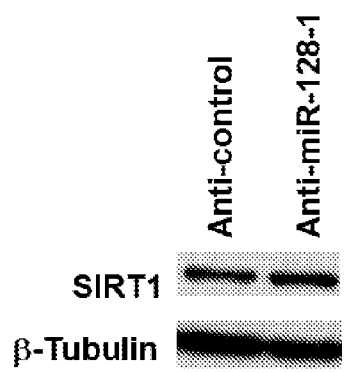
FIGS. 10A-B are each immunoblots showing that introduction of antisense oligonucleotides complementary to human miR-128-1 into human HepG2 liver cells causes increased expression of SIRT1 (10A), and introduction of human miR-128-1 precursor oligonucleotides into HepG2 cells results in decreased expression of SIRT1 (10B).
Figure 10B:
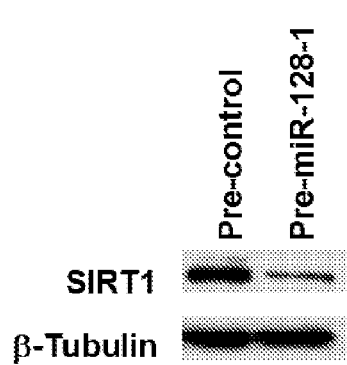
Figure 11A:
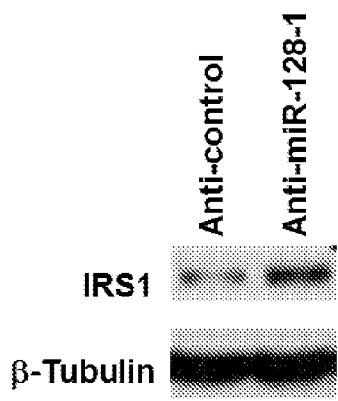
FIGS. 11A-C are immunoblots showing regulation of IRS1 and CYP39A1 expression by miR-128-1. Introduction of antisense oligonucleotides complementary to human miR-128-1 into HepG2 cells causes increased expression of IRS1 (11A), and introduction of human miR-128-1 precursor oligonucleotides into HepG2 cells causes decreased expression of IRS1 (11B) and decreased expression of CYP39A1 (11C).
Figure 11B:
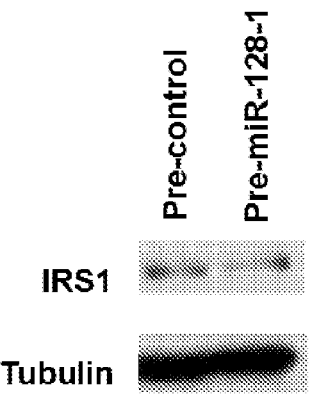
Figure 11C:
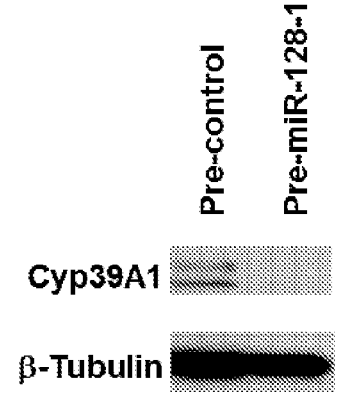

The bioinformatics analyses and experimental evidence presented herein that miR-128-1 targets genes involved in cholesterol/lipid homeostasis and insulin signaling/energy homeostasis, suggest that the R3HDM1/miR-128-1 genomic locus may harbor a "thrifty" gene whose elevated expression would allow increased fat storage/energy conservation in the face of starvation, thus providing a survival advantage in lean times. However, increased activity of such a thrifty gene (or thrifty microRNA in this case) would also cause excess fat storage when food/energy resources are plenty, and could potentially contribute to Metabolic Syndrome, type 2 diabetes, and cardiovascular disease (CVD) in a subset of human populations harboring predisposing SNP alleles.

The evidence indicates that the miR-128-1 microRNA may target a number of key regulators of cholesterol/lipid homeostasis and insulin signaling/energy homeostasis see Table 1); validation evidence presented herein demonstrate regulation of genes including the low-density lipoprotein receptor (LDLR), the ATP-binding cassette A1 transporter (ABCA1)

which is critical for high-density lipoprotein (HDL) synthesis and reverse cholesterol transport, the key regulator of lipid/energy homeostasis SIRT1, the insulin signaling intermediate IRS1, and the CYP39A1 enzyme which converts cholesterol to bile for biliary excretion.

TABLE 1

Predicted targets of miR-128-1 involved in cholesterol/lipid homeostasis and insulin signaling based on TargetScan Software Program. Shown in bold are genes verified as miR-128-1 targets in experiments.
Cholesterol & Fatty acids Homeostasis Target genes

| | | | |
|---|---|---|---|
| LDL receptors and associated proteins | LDLR LDLRAP1 PCSK9 CXCL16 LRP6 STAB2 COLEC12 | IRS1 INSR INSM1 IGF1 IGFR1 IGF2BP3 SIRT1 | Insulin Signaling |
| Cholesterol Transport | ABCA1 ABCG1 ApoF ApoOL ApoL6 ApoL2 ApoLD1 | FOXO1 PPARgamma PPARalpha PRKAA2 PRKAG2 LEP ADIPOQ | Fat/Lipid & Energy Key Regulatory Factors |
| Cholesterol/Lipid metabolism | FDFT1 DHCR24 LIPA LPIN1 OSBPL10 OSBPL2 OSBPL5 | | |
| Cholesterol Catabolism | Cyp39A1 Cyp7B1 Cyp8B1 | | |
| Fatty acid metabolism | ACAA2 FAR1 FAR2 FADS1 ELOVL7 ELOVL6 ELOVL1 ELOVL2 | | |

Thus, described herein are methods using miR-128-1 antisense treatment, e.g., in subjects suffering from Metabolic Syndrome (e.g., high LDL, low HDL, high triglycerides, obesity, nonalcoholic fatty liver disease, insulin resistance, and/or hypertension), type 2 diabetes, and/or cardiovascular disease (CVD). Such treatment is expected to result in one or more of the following:

a. lowering of circulating LDL (due to increased clearance by elevated hepatic LDLR and CYP39A1);

b. increased HDL (due to elevated expression of ABCA1 in liver and peripheral tissues);

c. lowered triglycerides (due to increased hepatic expression of SIRT1 and improved insulin signaling);

d. decreased obesity (due to increased adipose expression of SIRT1, Leptin and adiponectin);

e. decreased insulin resistance and type 2 diabetes (due to improved insulin signaling caused by increased expression of INSR, IRS1, and ISL1);

f. ameliorated nonalcoholic fatty liver disease (due to increased hepatic expression of SIRT1); and/or g. decreased atherosclerosis/CVD (due to increased hepatic LDLR, ABCA1, SIRT1, and CYP39A1 expression, as well as increased ABCA1 expression in atherogenic macrophages/foam cells associated with increased cholesterol efflux and reverse cholesterol transport to the liver).

Because of the predicted and demonstrated impact of miR-128-1 on a number of key regulators of cholesterol/lipid homeostasis and insulin signaling/energy homeostasis, without wishing to be bound by theory, it is hypothesized that miR-128-1 may itself represent a central regulator of human metabolism rivaling transcription factors such as SREBPs, LXRs, PPARs, and CREB in governing diverse metabolic circuits.

Bioinformatic Identification of a Potential Role for miR-128

The miR-128-1 microRNA is located in intron 18 of the R3HDM1 gene on human chromosome 2. Single nucleotide polymorphisms (SNPs) in a roughly 1 Mb genomic region in and surrounding the R3HDM1/miR-128-1 locus have been associated with increased total cholesterol and LDL-cholesterol in genome-wide association studies (GWAS), including in the Framingham Heart Study and in a meta-analysis of 46 GWAS linking 95 genomic loci to various blood lipid parameters in >100,000 people. Ma et al., BMC Medical Genetics 11:55 (2010), identified multiple SNPs in a 1.23 Mb genomic region as significantly associated with high LDL, and total cholesterol in >6,000 participants in the Framingham Heart Study. Two of the SNPs (rs12465802 and rs4954280) are located in the miR-128-1 host gene R3HDM1 (including in intron 18, within about 2 Kb of miR-128-1); see Table 1 and FIG. 2 of Ma et al, Teslovich et al., Nature 466:707-713 (2010), performed GWAS of >100,000 individuals of European descent; among the 95 SNPs identified in their screen was a SNP (rs7570971) in the RAB3GAP1-R3HDM1-LCT locus; the SNP was associated with elevated total cholesterol (see Table 1 of Teslovich et al). Silander et al., PLoS One 3:e3615 (2008), found an association between variants in the lactase (LCT) gene within the RAB3GAP1-R3HDM1-LCT genomic locus and both total and LDL-cholesterol (e.g., rs4988235, rs6719488, rs619054, rs7412, rs4988235, and rs6719488, see Table 5 of Silander et al.). Haplotype analysis implied that the associated variants are in the LCT gene itself, and not necessarily related to the lactase persistence variant upstream of the gene. The C of the exonic variant rs2304371, which was associated with highest cholesterol values, is the ancestral allele, present in other mammals and located in a highly conserved region.

Many SNPs in this genomic locus have also been linked to natural selection in a number of human populations irrespective of geographic location, Sabeti et al., Nature 449:913-8 (2007), identified the RAB3GAP1-R3HDM1-LCT genomic locus as positively selected during human evolution. 24 SNPs were identified in this 2.4 Mb genomic locus based on the fulfillment of two criteria: (1) selected alleles detectable by the tests are likely to be derived (newly arisen), because long-haplotype tests have little power to detect selection on standing (pre-existing) variation; the study was therefore focused on derived alleles, as identified by comparison to primate outgroups; (2) selected alleles are likely to be highly differentiated between populations, because recent selection is probably a local environmental adaptation; the study thus looked for alleles common in only the population(s) under selection. Muiños-Gimeno et al., Eur. J. Hum. Genet. 18; 218-26 (2010), investigated the possible association of 325 distinct human microRNAs with predisposition to disease. SNP coverage analysis revealed a lower SNP density in miRNAs compared with the average of the genome, with only 24 SNPs located in the 325 miRNAs studied. Further genotyping of 340 unrelated Spanish individuals showed that more than half of the SNPs miRNAs were either rare or monomorphic, in agreement with the reported selective constraint on human miRNAs. A comparison of the minor allele frequencies between Spanish and HapMap population samples confirmed the applicability of this SNP panel to the study of complex disorders among the Spanish population, and revealed two miRNA regions, hsa-mir-26a-2 in the CTDSP2 gene and hsa-mir-128-1 in the R3HDM1 gene, showing geographical allelic frequency variation among the four HapMap populations, probably because of differences in natural selection. The Bovine HapMap Consortium, Science 324:528-32 (2009), revealed a link of SNPs in the R3HDM1 genomic locus (e.g., rs29021800) to intramuscular fat (marbling) and "feed efficiency", i.e. cattle with this genotype have likely been selected for the trait to thrive on less feed; they consume less energy per amount of food given. This is a hallmark of a proposed "thrifty gene."

However, the fact that in addition to several genes this locus harbors a microRNA with targets that participate in regulation of cholesterol/lipid/energy homeostasis was not previously noted. MicroRNAs (miRNAs) are a class of small (e.g., 18-24 nucleotides) non-coding RNAs that exist in a variety of organisms, including mammals, and are conserved in evolution, miRNAs are processed from hairpin precursors of about 70 nucleotides which are derived from primary transcripts through sequential cleavage by the RNAse III enzymes drosha and dicer. Many microRNAs can be encoded in intergenic regions, hosted within introns of pre-mRNAs or within ncRNA genes. Many miRNAs also tend to be clustered and transcribed as polycistrons and often have similar spatial temporal expression patterns. MiRNAs have been found to have roles in a variety of biological processes including developmental timing, differentiation, apoptosis, cell proliferation, organ development, and metabolism.

Methods of Treatment

The methods described herein include the inhibition miR-128 in a subject who has cholesterol/lipid abnormalities (e.g., elevated circulating LDL, low HDL, elevated triglycerides), and/or is insulin resistant, and/or has the metabolic syndrome, and/or is suffering from type 2 diabetes, and/or cardiovascular disease. This can be achieved, for example, by administering an inhibitory nucleic acid, e.g., an antisense oligonucleotide that is complementary to miR-128, including but not limited to an antisense oligonucleotide comprising all or part of AAAGAGACCGGTTCACTGTGA (SEQ ID NO:7); in some embodiments, as described in farther detail below, the oligo includes different modifications, e.g., in the sugar backbone, to make it more cell permeable and nuclease resistant on one hand, and physiologically non-toxic at low concentrations on the other. Other inhibitory nucleic acids for use in practicing the methods described herein and that are complementary to miR-128 can be those which inhibit post-transcriptional processing of miR-128, such as an interfering RNA, including but not limited to an shRNA or siRNA, or an antagomir.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target nucleic acid (i.e., miR-128, e.g., all or part of any of SEQ ID NOs:1-6) and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In some embodiments, the inhibitory nucleic acids are designed to target a specific region of miR-128. For example, a specific functional region can be targeted, e.g., a region comprising a seed sequence or a region complementary to the target nucleic acid on which the miR-128 acts. For example, the inhibitory nucleic acid can be designed to target nucleotides 2-10 of the mature miR-128-1, e.g., complementary to CACAGUGAA, e.g., have the sequence TTCACTGTG (SEQ ID NO:9, which is the same as nucleotides 12-20 of SEQ ID NO:7). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., Mol. Biol., 1990, 215, 403-410; Zhang and Madden, Genome Res., 1997, 7, 649-656), e.g., using the default parameters.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sultanate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n CH_3$, $O(CH_2)n NH_2$ or $O(CH_2)n CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O-$CH_2CH_2OCH_3$, also known as 2'-O-(2-methoxyethyl)](Martin et al, Helv. Chim. Acta, 1995, 78, 486). Other preferred modifications include 2'-methoxy (2'-O-$CH_3$), 2'-propoxy (2'-$OCH_2CH_2CH_3$) and 2'-fluoro (2T-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally, or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me—C), 5-hydroxymethylcytosine (HMC), glycosyl HMC and gentobiosyl HMC, as well as synthetic nucleobases, e.g., 2-aminoadenine, 2-(methylamino)adenine, 2-(imidazolyalkl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, C., et al. Nucl. Acids Res. 1987, 15:4513). A "universal" base known in the art, e.g., inosine, can also be included. 5-Me—C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are hound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine, and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Leblett, B, ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let. 1994, 4, 1053-1060), a thioether, e.g., hexyl-S-tritylthiol (Manoharan et al, Ann. N.Y. Acad., Sci., 1992, 660, 306-309; Manoharan et al., Bioorg, Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluorescents, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, dodecandiol or undecyl residues, a phospholipid, e.g., dihexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to all or part of miR-128, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miR-128 sequence, then the bases are considered to be complementary to each other at that position. 100% complementarity is not required.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. The inhibitory nucleic acids and the miR-128 are complementary to each other when a sufficient number of corresponding positions in each molecule are occupied by nucleotides that can hydrogen bond with each other. Thus, "specifically hybridizable" and "complementary" are terms which are used to indicate a sufficient degree of complementarily or precise pairing such that stable and specific binding occurs between the inhibitory nucleic acid and the miR-128 target sequence. For example, if a base at one position of an inhibitory nucleic acid is capable of hydrogen bonding with a base at the corresponding position of a miR-128 molecule, then the bases are considered to be complementary to each other at that position.

Although in some embodiments, 100% complementarity is desirable, it is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target miR-128 molecule interferes with the normal function of the target miR-128 to cause a loss of activity, and there is a sufficient degree of complementarity to avoid non-specific binding of the sequence to non-target miR-128 sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42" C. in 15 nM NaCl, 1.5 mM trisodium citrate, and 0.1% SDS. In a more preferred embodiment, wash steps will occur at 68° C. in 15 mM NaCl, 1.5 trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within miR-128 (e.g., a target region comprising the seed sequence). For example, an antisense compound in which 18 of 20 nucleobases of the antisense oligonucleotide are complementary, and would therefore specifically hybridize, to a target region would represent 90 percent complementarily. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to a miR-128 target sequence are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a miR-128 target sequence. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxgygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs.

The LNA molecules can include molecules comprising 10-30, 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a miR-128 target sequence. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA (or any other inhibitory nucleic acid described herein); for example, a series of oligonucleotides of 10-30 nucleotides spanning the length of a target miR-128 sequence can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-A46 (2004); Kauppinen et al., Drug Disc. Today 2(3):287-290 (2005); and Ponting et al., Cell 136(4):629-641 (2009), and references cited therein.

In some embodiments of the methods described herein, the inhibitory nucleic acid is or comprises TTCACTGTG (SEQ ID NO:9), wherein all of the nucleic acids are locked and the backbone is a phosphorothioate backbone.

Antagomirs

In some embodiments, the antisense is an antagomir. Antagomirs are chemically modified antisense oligonucleotides that target a miR-128 target sequence. For example, an antagomir for use in the methods described herein can include a nucleotide sequence sufficiently complementary to hybridize to a miR-128 target sequence of about 12 to 25 nucleotides, preferably about 15 to 23 nucleotides.

In general, antagomirs include a cholesterol moiety, e.g., at the 3'-end. In some embodiments, antagomirs have various modifications for RNase protection and pharmacologic properties such as enhanced tissue and cellular uptake. For example, In addition to the modifications discussed above for antisense oligos, antagomir can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomir can include six phosphorothioate backbone modifications; two phosphorothioates are located at the 5'-end and four at the 3'-end. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008). Antagomirs useful in the present methods can also be modified with respect to their length or otherwise the number of nucleotides making up the antagomir. The antagomirs must retain specificity for their target, i.e., must not directly bind to, or directly significantly affect expression levels of transcripts other than the intended target.

In some embodiments, the inhibitory nucleic acid is locked and includes a cholesterol moiety (e.g., a locked antagomir).

siRNA/shRNA

In some embodiments, the nucleic acid sequence that is complementary to miR-128 can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target, Ribozymes Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave miR-128 within the background of cellular RNA. Such a cleavage event renders the miR-128 non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution strategies (Orgel, 1979. Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261: 1411-1418; Szostak, 1993, TIBS 17, 89-93; Kumar et al, 1995, FASEB J., 9, 1183; Breaker, 1996, Curr. Op. Biotech., 1, 442)

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning: A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target miR-128.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716, 928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean so lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL, sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or a therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy*, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy*, 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected antagomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-anti-miR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Methods of Treatment

Also described herein are methods that can also be used to treat subjects who have elevated triglycerides; are obese (BMI of 30 or higher), pre-diabetic or diabetic; or who have the metabolic syndrome; thus, the methods can include detecting the presence of one of these conditions, or diagnosing the subject with one of these conditions. In some embodiments, the methods include detecting the presence of a genetic variant affecting miR-128 levels, and optionally selecting subjects on the basis of the presence of such a variant.

Genetic Variants Affecting miR-128 Levels

In addition, the methods can also include identifying subjects for treatment using a method described by detecting one or both of (i) the presence of a genetic variation that predisposes a subject to elevated miR-128 levels, or (ii) the presence of elevated miR-128 levels, e.g., in a sample comprising liver and/or white adipose cells or tissue, e.g., from a biopsy.

In some embodiments, detecting the presence of a genetic variation that predisposes a subject to elevated miR-128 levels includes detecting the identity of an allele of one, two or more of rs6730157, rs12465802, rs4954280, rs2322660, rs309180, rs632632, rs7570971, rs4988235, or rs6719488, wherein the presence of an allele that is associated with elevated levels of miR-128, or with increased risk of elevated lipid levels (e.g., as described in Ma et al., BMC Medical Genetics 11:55 (2010); Teslovich et al., Nature 466:707-713 (2010); and Silander et al., PLoS One 3:e3615 (2008)), indicates that the subject is predisposed to have elevated levels of miR-128, and thus would benefit from the treatment methods described herein. In some embodiments, the methods include selecting a subject for treatment with a method described herein on the basis of the presence of an allele associated with elevated levels miR-128 or associated with increased risk of elevated lipid levels.

Elevated Cholesterol and/or Triglycerides

Abnormal cholesterol and triglyceride levels are associated with risk of disease, including cardiovascular disease; in some embodiments, the subjects treated using the methods described herein have, or are at risk of developing, abnormal cholesterol and/or triglyceride levels. In some embodiments, the subjects have elevated LDL-cholesterol, elevated total cholesterol, and/or elevated triglyceride levels.

High Density Lipoprotein Low Density Lipoprotein (LDL) and Very Low Density Lipoprotein (VLDL) are the three major kinds of cholesterol that are monitored. Total cholesterol and cholesterol/HDL ratio can also be monitored.

The following tables provide information regarding levels of cholesterol that are considered to be optimal (i.e., associated with a low or normal risk of cardiovascular disease) or abnormal (i.e., associated with a higher risk of cardiovascular disease). The numbers are in milligrams per deciliter (mg/dL).

Elevated levels of LDL are associated with increased risk of cardiovascular disease.

| LDL Cholesterol | LDL-Cholesterol Category |
|---|---|
| Less than 100 | Optimal |
| 100-129 | Near optimal/above optimal |
| 130-159 | Borderline high |
| 160-189 | High |
| 190 and above | Very high |

In the presence of cardiovascular disease, some experts consider optimal LDL levels to be less than 70. For people with diabetes or other multiple risk factors for heart disease, optimal levels of LDL are less than 100.

Increased levels of HDL cholesterol are associated with decreased risk of cardiovascular disease.

| HDL Cholesterol | HDL-Cholesterol Category |
|---|---|
| 60 and above | High; Optimal; lower risk of cardiovascular disease |
| Less than 40 in men and less than 50 in women | Low; increased risk factor of cardiovascular disease |

Total blood cholesterol is a measure of LDL cholesterol, HDL cholesterol, and other lipid components combined. Total cholesterol levels below 200 are desirable.

| Total Cholesterol | Category |
|---|---|
| Less than 200 | Desirable |
| 200-239 | Borderline High |
| 240 and above | High |

Triglyceride (triacylglycerol, TAG or triacylglyceride) is an ester derived from glycerol and three fatty acids, and is the main constituent of vegetable oil and animal fats (Nelson, D. L.; Cox, M. M. Lehninger, *Principles of Biochemistry*, 3rd Ed. Worth Publishing: New York, 2000).

The American Heart Association has set guidelines for triglyceride levels (after fasting for 8-12 hours), as follows:

| Level (mg/dL) | Level (mmoL/L) | Interpretation |
|---|---|---|
| <150 | <1.69 | Normal range, low risk |
| 150-199 | 1.70-2.25 | Borderline high |
| 200-499 | 2.26-5.65 | High |
| >500 | >5.65 | Very high: high risk |

Fasting triglyceride levels can be determined using any means known in the art, e.g., enzymatically using a glycerol kinase reaction-based colorimetric assay. Cholesterol levels can also be determined using any means known in the art, e.g., using immunoassay, electrophoresis, NMR, and/or precipitation-based methods.

Diabetic and Pre-Diabetic Subjects

In some embodiments, the subjects treated by the methods described herein have diabetes, i.e., are diabetic. A person who is diabetic has one or more of a Fasting Plasma Glucose Test result of 126 mg/dL or more; a 2-Hour Plasma Glucose Result in an Oral Glucose Tolerance Test of 200 mg/dL or more; and blood glucose level of 200 mg/dL or above. In some embodiments, the subjects treated by the methods described herein are being treated for diabetes, e.g., have been prescribed or are taking insulin, meglitinides, biguanides, thiazolidinediones, or alpha-glucosidase inhibitors.

In some embodiments the subjects are pre-diabetic, e.g., they have impaired glucose tolerance or impaired fasting glucose, e.g., as determined by standard clinical methods such as the intravenous glucose tolerance test (IVGTT) or oral glucose tolerance test (OGTT), e.g., a value of 7.8-11.0 mmol/L two hours after a 75 g glucose drink for impaired glucose tolerance, or a fasting glucose level (e.g., before breakfast) of 6.1-6.9 mmol/L.

The pathogenesis of type 2 diabetes is believed to generally involve two core defects: insulin resistance and β-cell failure (Martin et al., Lancet 340:925-929 (1992); Weyer et al., J. Clin. Invest. 104:787-794 (1999); DeFronzo et al., Diabetes Care. 15:318-368 (1992)). Important advances towards the understanding of the development of peripheral insulin resistance have been made in both animal models and humans (Bruning et al., Cell 88:561-572 (1997); Lauro et al., Nat. Genet. 20:294-298 (1998); Nandi et al., Physiol. Rev. 84:623-647 (2004); Sreekumar et al., Diabetes 51:1913-1920 (2002); McCarthy and Froguel, Am. J. Physiol. Endocrinol. Metab. 283:E217-E225 (2002); Mauvais-Jarvis and Kahn, Diabetes, Metab. 26:433-448 (2000); Petersen et al., N. Engl. J. Med. 350:664-671 (2004)). Thus, those subjects who have or are at risk for insulin resistance or impaired glucose tolerance are readily identifiable, and the treatment goals are well defined.

In some embodiments, the methods described herein include selecting subjects who have diabetes or pre-diabetes. In some embodiments, the following table is used to identify and/or select subjects who are diabetic or have pre-diabetes, i.e., impaired glucose tolerance and/or impaired fasting glucose.

| Fasting Blood Glucose | |
|---|---|
| From 70 to 99 mg/dL (3.9 to 5.5 mmol/L) | Normal fasting glucose |
| From 100 to 125 mg/dL (5.6 to 6.9 mmol/L) | Impaired fasting glucose (pre-diabetes) |
| 126 mg/dL (7.0 mmol/L) and above on more than one testing occasion | Diabetes |
| Oral Glucose Tolerance Test (OGTT) [except pregnancy] (2 hours after a 75-gram glucose drink) | |
| Less than 140 mg/dL (7.8 mmol/L) | Normal glucose tolerance |
| From 140 to 200 mg/dL (7.8 to 11.1 mmol/L) | Impaired glucose tolerance (pre-diabetes) |
| Over 200 mg/dL (11.1 mmol/L) on more than one testing occasion | Diabetes |

Body Mass Index (BMI)

Obesity increases a subject's risk of developing T2D. BMI is determined by weight relative to height, and equals a person's weight in kilograms divided by height in meters squared (BMI=kg/m$^2$). Accepted interpretations are given in the following table:

| Category | BMI |
| --- | --- |
| Underweight | ≤18.5 |
| Normal weight | 18.5-24.9 |
| Overweight | 25-29.9 |
| Obese | ≥30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above (i.e., obese subjects).

Metabolic Syndrome

In some embodiments, the methods include determining whether a subject has the metabolic syndrome, and selecting the subject if they do have the metabolic syndrome, then administering an inhibitory nucleic acid as described herein. Determining whether a subject has the metabolic syndrome can include reviewing their medical history, or ordering or performing such tests as are necessary to establish a diagnosis.

The metabolic syndrome, initially termed Syndrome X (Reaven, Diabetes, 37(12):1595-1607 (1988)), refers to a clustering of obesity, dyslipidemia, hypertension, and insulin resistance. All components of the metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low HDL (e.g., less than 40 mg/dL for men, and less than 50 mg/DL for women), elevated LDL (e.g., above 130 mg/dL), high blood pressure (e.g., greater than or equal to 130/85 mmHg) and/or elevated fasting glucose (e.g., greater than or equal to 110 mg/dL). In some embodiments, levels of these criteria may be higher or lower, depending on the subject; for example, in subjects of Asian ancestry; see, e.g., Meigs, Curr. Op. Endocrin. Diabetes, 13(2):103-110 (2006). A determination of the presence of metabolic syndrome can be made, by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA. 287(3):356-359 (2002)). Insulin resistance is now felt to be central in the pathogenesis of these related disorders.

Nonalcoholic fatty liver disease (NAFLD) and its most severe form, nonalcoholic steatohepatitis (NASH), are associated with high fat diet, high triglyceride levels, obesity, the metabolic syndrome and type 2 diabetes, and pose an increased risk of cardiovascular disease. NAFLD is an accumulation of fat in the liver that is not a result of excessive consumption of alcohol. 15% to 25% of cases of NAFLD progress and are associated with inflammation and liver damage; this condition is referred to as NASH. NASH is associated with an increased risk of developing liver cirrhosis and subsequence complications, including hepatocellular carcinoma. A diagnosis of NAFLD or NASH can be made by methods known in the art, e.g., by histological examination of liver biopsy samples.

EXAMPLES

The invention is further described in the following examples, which do not limit the scope of the invention described in the claims.

Example 1

A Functional Role of miR-128 in Lipid Homeostasis and Insulin Signaling

To determine whether miR-128 plays a role in lipid homeostasis and insulin signaling, the following experiments were performed. First, expression of miR-128-1 was evaluated in 20 selected human tissues using the Taqman miRNA Assay Kit (Applied Biosystems). Total RNA samples were purchased from Ambion, now an Applied Biosystems company. Briefly, 10 ng total RNA was reverse-transcribed using a miR-128-specific primer (comprising sequence complementary to part of SEQ NO:3), followed by quantitative real-time PCR with Taqman probes. Thereby, the U6 spliceosomal RNA was used as an internal control. The results indicated that miR-128-1 was co-expressed with the host gene R3HDM1 in a number of human tissues (FIGS. 7A-B). Both genes were shown to be expressed fairly ubiquitously. The function of R3HDM1 has not yet been determined. The expression profile of miR-128 shown in FIG. 8B reflects the combined expression of miR-128-1 (located in the R3HDM1 gene) and miR-128-2, whose genomic location is within the ARPP-21 host gene. miR-128-1 and miR-128-2 have identical mature sequences, which are measured here.

To further determine whether miR-128 plays a role in regulating lipid homeostasis and insulin signaling, experiments were performed to see what effect increased or decreased expression of miR-128 would have on genes associated with lipid homeostasis, including LDLR, ABCA1, SIRT1, and CYP39A1, as well as the insulin-signaling component IRS1. Mutations in LDLR cause the autosomal dominant disorder familial hypercholesterolemia (Brown and Goldstein, Scientific American. 1984, 252:52-60; Leigh S E et al. Ann Hum Genet. 2008, 72:485-498). With cholesterol as its substrate, the ABCA1 protein functions as a cholesterol efflux pump in the cellular lipid removal pathway, thereby promoting HDL biosynthesis. Mutations in the ABCA1 gene have been associated with Tangier's disease, familial high-density lipoprotein deficiency, and elevated cardiovascular disease risk (Brooks-Wilson et al., (1999) Nature Genetics, 22:336-45; Hong et al., (2003) Atherosclerosis 164: 245-250). The CYP39A1 enzyme contributes to the cholesterol catabolic pathway in the liver, which converts cholesterol to bile acids, the primary mechanism for the removal of excess cholesterol from the body. Mutations in this CYP sub-family of enzymes are associated with defects in bile acid biosynthesis which can eventually lead to severe metabolic disorders (Wang et al., (2009) J Lipid Res. 50:S406-411). SIRT1 regulates the function of many key transcription factors in human metabolism. For example, it inhibits SREBP activity, a master regulator of cholesterol and fat metabolism (Walker et al., (2010) Genes Dev. 24:1403-1417):

IRS1 plays a key role in transmitting signals from the insulin receptor to intracellular metabolic pathways. Mutations in the IRS1 gene are associated with type II diabetes and susceptibility to insulin resistance (Berger et al. (2002), Diabet Med. 19:804-809; Eftychi C et al. (2004) Diabetes: 53:870-873):

The effects of increasing expression of miR-128 were evaluated by the introduction of excess miR-128-1 precursor oligonucleotides into human HepG2 liver cells. The precursor oligonucleotides were double stranded and mimicked the precursor sequence of miR-128. The active strand comprises the sequence ID NO.3. Antisense treated cells were harvested 24 hours after transfection, whereas cells treated with Precursor oligonucleotides were harvested after 48 hours of transfection in whole cell extract buffer. Immunoblotting was carried out using protein specific antibodies according to manufacturer's protocol. Antibodies for LDLR, ABCA1 and CYP39A1 were from Abcam. SIRT1 antibody was from Cyclex, and the antibody for IRS1 from Cell Signaling.

As shown in FIGS. 8-11, increasing expression of miR-128 results in decreased expression of key cholesterol/lipid regulators such as LDLR, ABCA1, SIRT1, and CYP39A1, well as the insulin-signaling component IRS1.

Next, the effects of decreasing expression of miR-128 were evaluated by the introduction of excess miR-128-1 antisense oligonucleotides into human HepG2 liver cells. The antisense oligos were purchased from Ambion (Applied Biosystems). Transfection studies were all carried out by electroporation using cell-specific transfection reagents from Lonza Company. Each transfection procedure contained 2×10$^6$ HepG2 cells and 0.1 nmol of antisense oligo. Upon transfection, cells were plated on polylysine-coated plates and harvested for analysis 24 hours post incubation at 37° C. under 5% CO2. Cells were all grown in MEM medium with 10% FBS. The antisense sequence used in this study was AAAGAGACCG-GTTCACTGTGA (SEQ ID NO:7). According to the manufacturer the oligo contains a phosphorothioate backbone and 2'-Methoxy moieties.

Importantly, reducing miR-128 expression using antisense oligonucleotides complementary to miR-128-1 cause increased expression of LDLR, ABCA SIRT1 and IRS1, suggesting that antisense-based therapeutics could potentially impact the levels of these proteins in human liver (FIGS. 8-11).

These results support a central role of miR-128-1 in regulation of Cholesterol/lipid homeostasis and insulin signaling/energy homeostasis.

Example 2 miR-128 Regulates Hepatic LDLR Expression and LDL Uptake

To determine whether miR-128 can directly affect expression of LDLR, a reporter construct was developed that included the LDLR-3' UTR sequence linked to a luciferase reporter. The construct contained the entire LDLR 3'UTR sequence (2498 bp) downstream of the Luciferase gene (RenSP). Transfections were carried out using the LIPO-FECTAMINE transfection reagent. HEK293 cells were transfected with 10 ng of plasmid construct and 30 nM of Precursor miR-128 oligos, and the Luciferase actvity was measured 24 hours post-transfection. A beta-Galactosidase expression vector was cotransfected (100 ng) and its activity used as a normalizer.

Figure 12A:
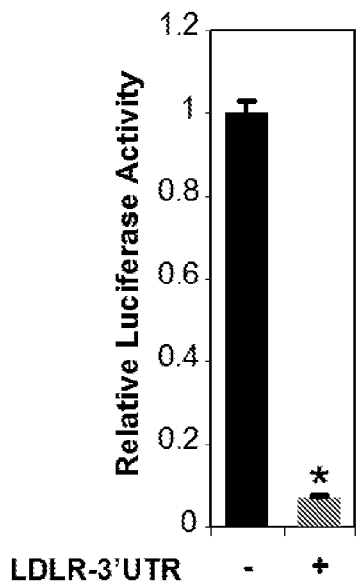
FIGS. 12A-B are bar graphs showing miR-128-1 target validation at LDLR-3'UTR. Insertion of the LDLR-3'UTR sequence into a Luciferase reporter construct results in strongly decreased luciferase expression in HEK293 cells, suggesting the presence of repressive regulatory motifs within the LDLR-3'UTR (12A). Introduction of human miR-128-1 causes further repression of the Luciferase-LDLR 3'UTR, showing that LDLR is specifically targeted by miR-128-1 through its 3' UTR (12B).
Figure 12B:
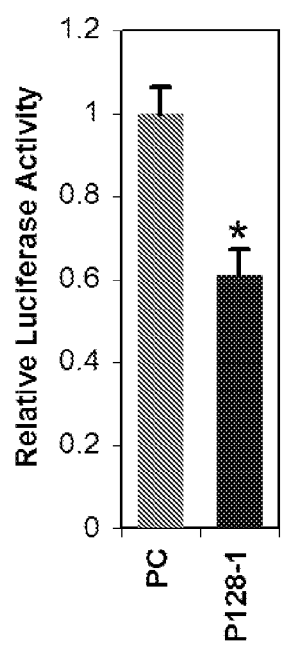

When expressed in HEK 293 cells, the LDLR 3'UTR mediated strong repression of the fused Luciferase reporter (FIG. 12A), and this repression was further increased upon introduction of additional miR-128-1 precursor oligonucleotides (FIG. 12B).

To determine whether miR-128 had any effects on lipid uptake, human liver cells (HepG2) were treated with the antisense and precursor oligos as described above. The LDL uptake experiment was initiated by adding DiI-LDL (Biomedical Technologies) in a final concentration of 10 µg/ml. The LDL uptake was carried out for 2 hours. Upon incubation, cells were washed three times with cold PBS. Cells were finally lysed in SS buffer containing 0.1 M NaOH and 0.1% SDS according to standard protocols (Stephan Z F & Yurachek E C, (1993) J Lipid Res 34: 325-330).

As in the HE293 cells, LDL uptake into human liver cells (HepG2) was increased upon treatment with miR-128-1 antisense oligonucleotides, and decreased upon treatment with miR-128-1 precursor oligonucleotides (FIGS. 8A-B and 14A-C). These results clearly show that miR-128-1 has functional effects on LDLR activity by post-transcriptional regulation of the expression of LDLR.

These data together provide critical support for the notion that miR-128-1 is an important regulator of hepatic LDLR expression and LDL uptake. Indeed, miR-128-1 is the first significant regulator of LDLR expression since the discovery of the SREBP genes 17 years ago by Brown and Goldstein at UT Southwestern Medical Center in Dallas (Yokoyama et al., (1993) Cell, 75:187-195; Goldstein and Brown, (2009) Arterioscler Thromb Vasc Biol. 29:431-438).

Example 3 miR-128-1 Regulates Expression of the ATP-binding cassette A1 (ABCA1) Cholesterol Transporter and SIRT1

The ABCA1 cholesterol transporter is another potential target of miR-128-1 (Table 1). ABCA1 is critical for the production of HDL by the liver, and also acts as a cholesterol efflux pump that extrudes cholesterol and phospholipids to HDL from peripheral tissues and cells, including arterial macrophages, to promote reverse cholesterol transport (RCT) (Cuchel and Rader, Circulation 113 (21), 2548-2555 (2006)). Importantly, variations in the ABCA1 gene have been linked to impaired HDL synthesis and RCT, and may be associated with elevated risk for atherosclerosis (Rader et al., J Lipid Res 50 Suppl, S189-194 (2009)).

SIRT1 regulates the function of many key transcription factors in human metabolism. For example, it inhibits SREBP activity, a master regulator of cholesterol and fat metabolism (Walker et al., (2010) Genes Dev. 24:1403-1417).

Figure 13A:
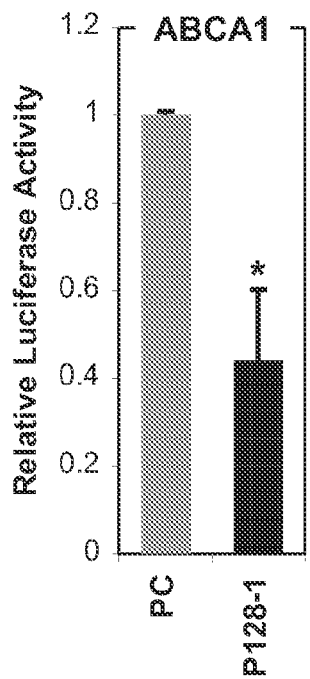
FIGS. 13A-B are bar graphs showing that MiR-128-1 targets the ABCA1 (13A) and SIRT1 (13B) 3' UTRs for post-transcriptional regulation. Introduction of human miR-128-1 causes a repression of of the Luciferase-ABCA1 and SIRT1 3'UTRs, showing specific targeting by miR-128-1 through their 3'UTR.
Figure 13B:
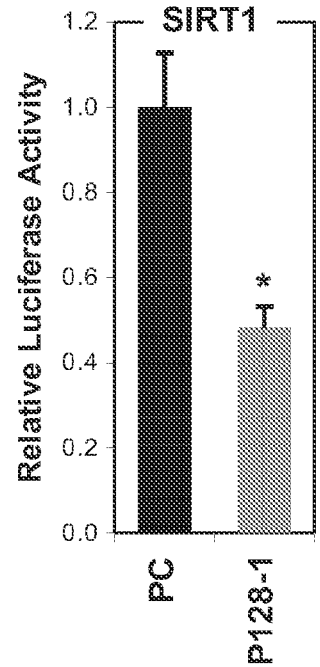
Figures 14A, 14B:
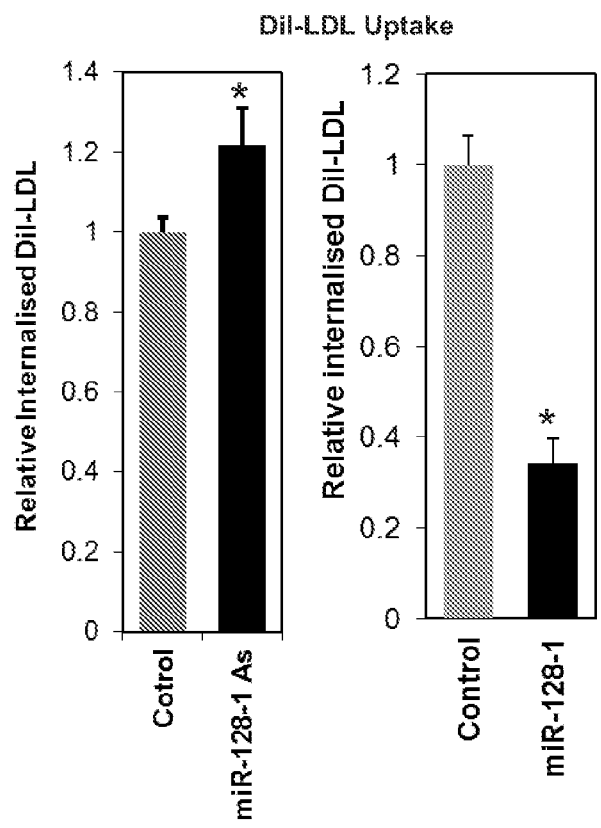
FIGS. 14A-B are bar graphs showing that miR-128-1-mediated regulation of LDL receptor expression affects LDL uptake in human hepatoma cells. Fluorescently labeled (Dil) LDL uptake is strongly reduced upon treatment of human HepG2 hepatoma cells with miR-128-1 precursors (14A), whereas a modest but significant increase in Dil-LDL uptake is observed after miR-128-1 antisense treatment (14B). All experiments were repeated at least three times.

To determine whether miR-128 can directly affect expression of ABCA1 and SIRT1, reporter constructs were developed that included either the ABCA1-3' UTR and SIRT1-3' UTR sequence linked to a luciferase reporter. The constructs contained the SIRT1 or ABCA1 3'UTR sequences downstream of the Luciferase gene (RenSP). Pre-plated HEK293 cells were transfected with 40 nM miR-128-1 precursor or precursor control (Ambion) in the presence of 2 ng of ABCA1 or SIRT1 luciferase plasmid constructs, respectively, using lipofectamine 2000 (Invitrogen/Life Technologies). Cells were harvested 24-48 hours post-transfection and the luciferase activity measured following standard protocols (Promega). The results show that miR-128-1 targets the ABCA1 and SIRT1 3' UTRs for post-transcriptional regulation. Introduction of human miR-128-1 causes a repression of of the Luciferase-ABCA1 (FIG. 13A) and SIRT1 (FIG. 13B) 3'UTRs, showing specific targeting by miR-128-1 through their 3'UTR.

Figure 15:
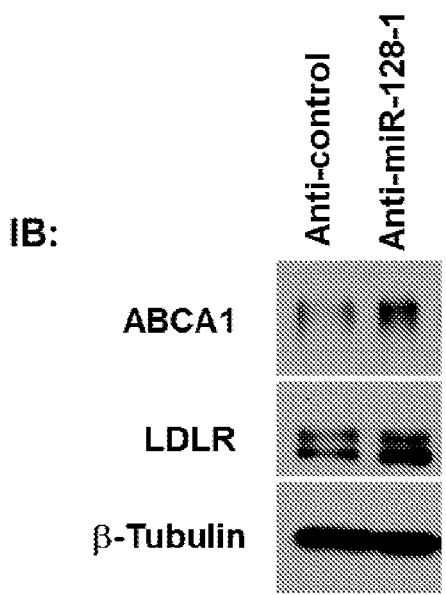
FIG. 15 is an immunoblot showing that miR-128-1 regulates ABCA1 and LDLR, which are involved in cholesterol/lipid and energy homeostasis, in the human liver cell line Huh-7. miR-128-1 antisense treatment of Huh-7 cells resulted in elevated expression of ABCA1 and LDLR. Beta-tubulin was used as negative control.

To further evaluate the effects of miR-128-1 ABCA1 expression, Huh-7 cells were treated with 50 nM of Anti-miR-128-1 (Ambion) and plated at high density in DMEM media containing 5% FBS. After 48 hrs cells were harvested and protein amount was quantified by western blotting analysis. As shown in FIG. 15, coordinated up regulation of ABCA1 and LDLR in Huh-7 human liver cells was seen in response to miR-128-1 antisense inhibition. Thus, miR-128-1 indeed controls the levels of ABCA1 in human liver cells (FIG. 15).

Example 4

Effects of miR-128-1 on Human Liver Cell Whole Genome Expression

MicroRNAs typically regulate many targets, frequently by controlling mRNA stability[48]. TargetScan provides a mathematical predictor of microRNA targets. To explore the reach of miR-128-1 in cells empirically, DNA microarray analysis was employed to obtain a comprehensive list of potential miR-128-1 targets. These studies identify novel pathways regulated by miR-128-1 that may affect therapeutic targeting efforts. Samples were analyzed on Affymetrix human genome U133 Plus 2.0 arrays by Affymetrix readers. Statistical and bioinformatics analyses (e.g., Gene Ontology (GO) analysis (Osborne et al., Methods Mol Biol 377, 223-242 (2007)) and Ingenuity Pathway Analysis (Ganter and Giroux, Curr Opin Drug Discov Devel 11 (1), 86-94 (2008); Thomas and Bonchev, Hum Genomics 4 (5), 353-360 (2010))) were performed. Expression changes of selected genes of interest were confirmed by qRT-PCR.

Figure 16:
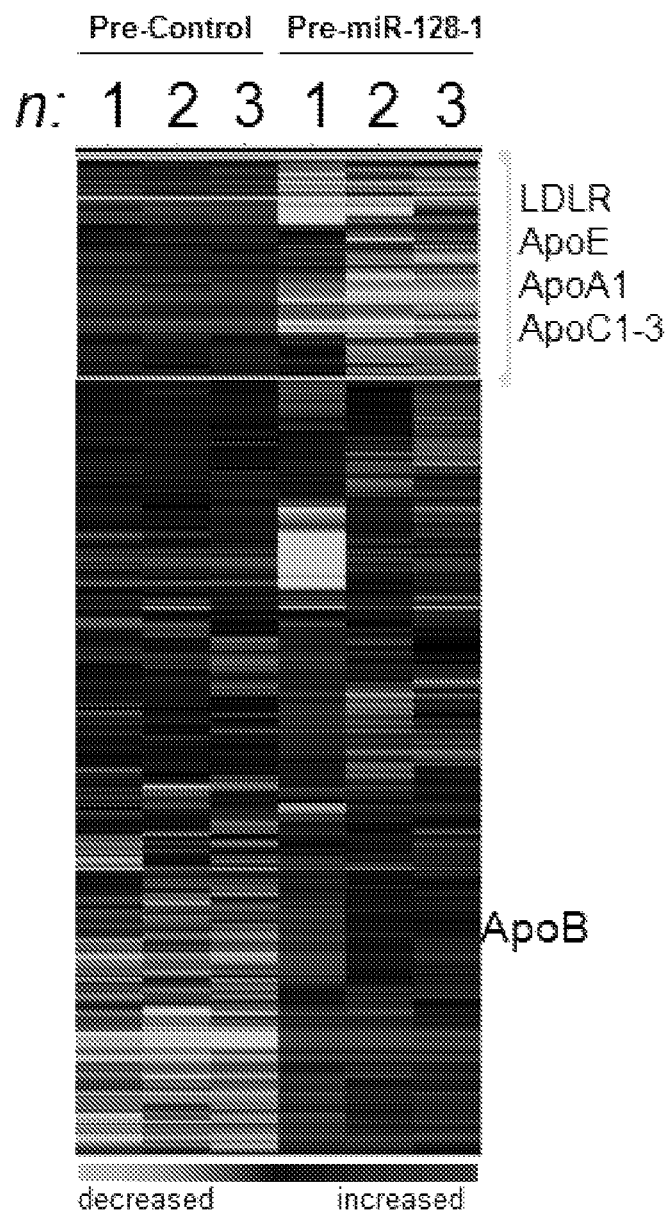
FIG. 16 shows the results of Genome-wide analysis of miR-128-1 biological effect on lipoprotein metabolism genes in HepG2 human liver cells. As expected, excess miR-128-1 decreases the level of its target gene LDLR, however, miR-128-1 also negatively affects the expression of major protein components of HDL lipoprotein particles such as ApoA1, ApoC1-3 and ApoE, indicating the disruptive role of miR-128-1 in proper lipid metabolism and trafficking. Interestingly, this indirect effect is extended to an induced expression of ApoB, a major component of VLDL and LDL lipoproteins ("bad cholesterol"). Unbiased hierarchical clustering analysis was applied to the DNA microarray data.

DNA microarray analysis of HepG2 cells transfected with miR-128-1 precursor oligonucleotides was performed. Unsupervised hierarchical clustering analysis revealed that several predicted and verified targets of miR-128-1, including LDLR and ABCA1, were indeed down-regulated as expected in miR-128-1-treated cell as compared with cells transfected with control oligonucleotides (FIG. 16). Unexpectedly, there was decreased expression of several additional genes involved in cholesterol/lipid trafficking, but which were not predicted as targets of miR-128-1, including ApoE, ApoA1, and several genes in the ApoC cluster (FIG. 16). Conversely, ApoB was found to be upregulated HepG2 cells with increased miR-128-1 levels. These initial findings suggest that miR-128-1 may coordinately control both directly and indirectly the production of key lipoproteins involved in cholesterol/lipid trafficking, with important relevance to cardiovascular biology. Indeed, ApoB is associated with pro-atherogenic LDL, whereas ApoA1 is associated with anti-atherogenic HDL (Walldius and Jungner, J. Intern Med 259 (5), 493-519 (2006)). In accord with this notion, unbiased Gene Ontology analysis of the entire DNA microarray dataset by DAVID revealed a highly statistically significant association with the "Cardiovascular Disease" and "Atherosclerosis" GO terms/gene sets.

Example 5

Functional Contribution of miR-128-1 to Control of Cholesterol/Lipid and Energy Homeostasis in Vivo It was hypothesized that miR-128-1 manipulation will affect lipid/cholesterol storage and energy usage in mice, and that the effects of miR-128-1 overexpression will be exacerbated by a high-fat diet while antisense treatment will provide protection from deleterious effects normally associated with this diet. In two independent experiments, C57BL/6J mice (n=10) were placed on a high-fat diet were treated with a lentivirus encoding for human miR-128-1 precursor obtained from System Biosciences Inc. (SBI). The modified pMIRNA1 consists of the native human miR-128-1 stem loop structure and 200-400 base pairs of upstream and downstream flanking genomic sequence (see FIG. 18, SEQ ID NO:8).

Mice were injected with $2-5\times10^7$ IFU/mouse of the lentiviral construct in 300 µl PBS via either retro-orbital or tail-vein injections. At days 9 (Exp. 1) and 14 (Exp. 2) after the injection, the mice were sacrificed and total blood was collected. The cholesterol distribution in plasma lipoproteins fractions was assessed by fast-performance liquid chromatography (FPLC) gel filtration using 250 µl of pooled serum.

Figure 17A:
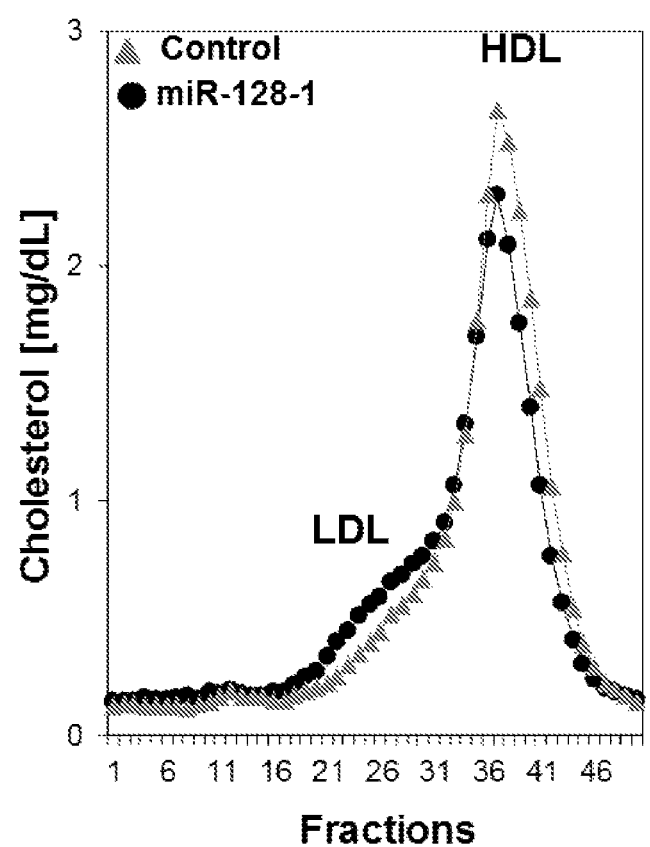

The mice overexpressing miR-128-1 exhibited several striking phenotypes. First, while these mice ate much less food (data not shown), their weight was very similar to controls (29.46+/−0.45 (s.e.m) grams {miR-128-1} vs. 30.59+/− 0.47 (s.e.m.) grams {control}, p=0.19, n=10 per group). This suggests that miR-128-1 indeed can increase the ability of an animal to maintain weight on a reduced number of calories, as the studies associating its locus with feed efficiency in cattle suggested. Second, serum profiling showed that LDL-cholesterol was raised and HDL-cholesterol lowered compared to control virus-injected mice (FIGS. 17A-B; pooled serum from 10 mice for each group). Thus the hypothesis regarding miR-128-1 effects on cholesterol trafficking has been validated in vivo. Third, visual inspection revealed that miR-128-1 overexpressing mice exhibited an unexpected and distinctive "greasy fur" phenotype. This initial experiment supports the feasibility of our approach and suggests that miR-128-1 overexpression may cause altered animal metabolism, possibly related to lipid homeostasis/fat storage.

Example 6

Effect of miR-128-1 Manipulations on Metabolic Homeostasis in Mice

These studies are expanded to include analyses of mice on different types of diets either overexpressing miR-128-1, or subjected to miR-128-1 antisense inhibition. First, twenty C57BL/6J mice on regular chow are subjected to tail-vein injection with a miR-128-1 lentivirus, e.g., as described above, while another twenty mice are injected with control (empty vector) virus. To determine the potential collaboration of elevated miR-128-1 expression with high-fat diets, similar in vivo experiments are performed with animals fed either a Western-type diet (41% of calories from fat), or a high-fat diet (60% of calories as fat).

The animals are weighed every three days. Food intake, and general health and activity, will be monitored daily. After 10 days, blood will be drawn and serum levels of total cholesterol, triglycerides, glucose, and liver enzymes (ALT/AST, for toxicity) will be analyzed. In addition, FPLC analysis of serum lipoproteins (LDL, HDL, and VLDL) will be carried out.

Next, the effects of miR-128-1 overexpression are "rescued" by an antisense approach, and the effects of inhibition of endogenous miR-128-1 are assessed. The twenty mice from each cohort above are divided into two groups, one receiving subcutaneous injection with 5 mg/kg of LNA-antisense oligonucleotides complementary to miR-128-1 (Exigon), while the other 10 mice receive injection with PBS (control). This LNA-antisense treatment regimen is similar to that we employed in a previous in vivo study of miR-33 (Nafaji-Shoushtari et al., Science 328 (5985), 1566-1569 (2010)). After one week, the mice are sacrificed and serum is collected, as well as liver and adipose tissues, for analysis as previously described.

OTHER EMBODIMENTS

It is to be understood that while the invention has been described in conjunction with the detailed description

What is claimed is:

1. A method of reducing obesity, treating or reducing predisposition to insulin resistance, and/or treating or reducing predisposition to type II diabetes, in a subject, the method comprising administering to the subject an inhibitory nucleic acid sequence that is complementary to all or part of any of SEQ ID NOs:1-6 in an amount sufficient to decrease obesity, treat or reduce predisposition to insulin resistance, and/or to treat or reduce predisposition to type II diabetes, thereby decreasing obesity, treating or reducing predisposition to insulin resistance, and/or treating or reducing predisposition to type II diabetes, in the subject.

2. The method of claim 1, wherein the inhibitory nucleic acid is complementary to all or part of SEQ ID NO:2.

3. The method of claim 1, wherein the inhibitory nucleic acid is complementary to at least nucleotides 2-7 (5'-CACAGU-3') of SEQ ID NO:3.

4. The method of claim 1, wherein the inhibitory nucleic acid is an antisense oligonucleotide.

5. The method of claim 4, wherein the antisense oligonucleotide comprises a sequence that is complementary to SEQ ID NO:3.

6. The method of claim 4, wherein the antisense oligonucleotide is an antagomir.

7. The method of claim 1, wherein the inhibitory nucleic acid is an interfering RNA.

8. The method of claim 7, wherein the interfering RNA is a small hairpin RNA (shRNA) or small interfering RNA (siRNA).

9. The method of claim 1, wherein the inhibitory nucleic acid sequence inhibits post-transcriptional processing of SEQ ID NO:1 or 5.

10. The method of claim 1, wherein the subject has metabolic syndrome or Type 2 diabetes.

11. The method of claim 10, further comprising selecting a subject on the basis that they have metabolic syndrome or Type 2 diabetes.

12. The method of claim 1, further comprising detecting the presence of one or more alleles associated with increased levels of miR-128 and/or predisposition to increased levels of serum lipids, and optionally selecting a subject on the basis of the presence of an allele associated with increased levels of miR-128.

13. The method of claim 1, further comprising selecting a subject who has a BMI of 25 or above.

14. The method of claim 1, wherein the inhibitory nucleic acid has at least one locked nucleotide.

15. The method of claim 1, wherein the inhibitory nucleic acid has a phosphorothioate backbone.

16. The method of claim 1, wherein the inhibitory nucleic acid decreases obesity in the subject.

17. The method of claim 1, wherein the inhibitory nucleic acid treats or reduces predisposition to insulin resistance in the subject.

18. The method of claim 1, wherein the inhibitory nucleic acid treats or reduces predisposition to type II diabetes in the subject.

19. The method of claim 1, wherein the inhibitory nucleic acid increases adipose expression of Sirtuin 1 (SIRT1).

20. The method of claim 1, wherein the inhibitory nucleic acid increases expression of Insulin receptor substrate 1 (IRS1).

* * * * *

SEQUENCE LISTING

```
<160> NUMBER OF SEQ ID NOS: 9

<210> SEQ ID NO 1
<211> LENGTH: 82
<212> TYPE: DNA
<213> ORGANISM: Homo sapiens

<400> SEQUENCE: 1
tgagctgttg gattcggggc cgtagcactg tctgagaggt ttacatttct cacagtgaac    60
cggtctcttt ttcagctgct tc                                             82

<210> SEQ ID NO 2
<211> LENGTH: 21
<212> TYPE: DNA
<213> ORGANISM: Artificial
<220> FEATURE:
<223> OTHER INFORMATION: synthetic oligonucleotide

<400> SEQUENCE: 2
tcacagtgaa ccggtctctt t                                              21

<210> SEQ ID NO 3
<211> LENGTH: 21
<212> TYPE: RNA
<213> ORGANISM: Artificial
<220> FEATURE:
<223> OTHER INFORMATION: synthetic oligonucleotide

<400> SEQUENCE: 3
ucacagugaa ccggucucuu u                                              21

<210> SEQ ID NO 4
<211> LENGTH: 82
<212> TYPE: RNA
<213> ORGANISM: Homo sapiens

<400> SEQUENCE: 4
ugagcuguug gauucggggc cguagcacug ucugagaggu uuacauuucu cacagugaac    60
cggucucuuu uucagcugcu uc                                             82

<210> SEQ ID NO 5
<211> LENGTH: 84
<212> TYPE: DNA
<213> ORGANISM: Homo sapiens

<400> SEQUENCE: 5
tgtgcagtgg aagggggggc cgatacactg tacgagagtg agtagcaggt ctcacagtga    60
accggtctct ttccctactg tgtc                                           84

<210> SEQ ID NO 6
<211> LENGTH: 84
<212> TYPE: RNA
<213> ORGANISM: Homo sapiens

<400> SEQUENCE: 6
ugugcagugg aagggggggc cgauacacug uacgagagug aguagcaggu cucacaguga    60
accggugugu uugggguacug ugcu                                          84

<210> SEQ ID NO 7
```

```
<211> LENGTH: 21
<212> TYPE: DNA
<213> ORGANISM: Artificial
<220> FEATURE:
<223> OTHER INFORMATION: synthetic oligonucleotide

<400> SEQUENCE: 7
aaagagaccg gttcactgtg a                                                  21

<210> SEQ ID NO 8
<211> LENGTH: 493
<212> TYPE: DNA
<213> ORGANISM: Artificial
<220> FEATURE:
<223> OTHER INFORMATION: synthetic oligonucleotide

<400> SEQUENCE: 8
tcactgcata taaggagtgt ggtatagtat aaagaaactt tctgcaggta gtaattatag         60
tgaagatttt aggtttacaa agccctagct gttttctgtg tagcttttat tattcttatg        120
actcttgaca agtttgtagc ttcaccatat acatttaata ttttgcaata attggccttg        180
ttcctgagct gttggattcg gggccgtagc actgtctgag aggtttacat ttctcacagt        240
gaaccggtct cttttcagc tgcttcctgg cttcttttta ctcaggtttc cactgctttt        300
ttgctttttt taatgctgta tgaaggtgtt aacatttgtt tatattttc attaattgta         360 ataccctttaa atcatgcatc atactcagaa atagggatta gaatttaagt gacatctttg        420
gcctaatata atttacctgt taaaaatttg tgaaagctat tgcttatttc ttttccaaag        480
tagatttgga tga                                                           493

<210> SEQ ID NO 9
<211> LENGTH: 9
<212> TYPE: DNA
<213> ORGANISM: Artificial
<220> FEATURE:
<223> OTHER INFORMATION: synthetic oligonucleotide

<400> SEQUENCE: 9 ttcactgtg                                                                 9
```